United States Patent
Verruto et al.

(10) Patent No.: US 11,434,493 B2
(45) Date of Patent: Sep. 6, 2022

(54) REGULATORY SEQUENCES FOR EXPRESSION OF TRANSGENES

(71) Applicant: Synthetic Genomics, Inc., La Jolla, CA (US)

(72) Inventors: John Verruto, San Diego, CA (US); Moena Aqui, San Diego, CA (US)

(73) Assignee: Viridos, Inc., La Jolla, CA (US)

( * ) Notice: Subject to any disclaimer, the term of this patent is extended or adjusted under 35 U.S.C. 154(b) by 0 days.

(21) Appl. No.: 17/167,921

(22) Filed: Feb. 4, 2021

(65) Prior Publication Data

US 2021/0238611 A1  Aug. 5, 2021

Related U.S. Application Data

(60) Provisional application No. 62/970,580, filed on Feb. 5, 2020.

(51) Int. Cl.
| | | |
|---|---|---|
| *C12N 15/79* | (2006.01) | |
| *C07K 14/405* | (2006.01) | |
| *C12N 1/12* | (2006.01) | |

(52) U.S. Cl.
CPC ............ *C12N 15/79* (2013.01); *C07K 14/405* (2013.01); *C12N 1/12* (2013.01)

(58) Field of Classification Search
CPC ...... C12N 15/79; C12N 1/12; C12N 15/8216; C07K 14/405
See application file for complete search history.

(56) References Cited

U.S. PATENT DOCUMENTS

| | | | |
|---|---|---|---|
| 6,812,339 B1 | 11/2004 | Venter et al. | |
| 2005/0196754 A1 | 9/2005 | Drmanac et al. | |
| 2013/0323780 A1* | 12/2013 | Schneider | C12N 15/111 |
| | | | 435/320.1 |
| 2014/0161721 A1 | 6/2014 | Hatchwell et al. | |
| 2018/0073076 A1 | 3/2018 | Hatchwell et al. | |

FOREIGN PATENT DOCUMENTS

WO  WO 2020/132036  6/2020

OTHER PUBLICATIONS

Weissman JC et al. High-selection produces a fast-growing Picochlorum celeri. Algal Research. 2018. 36:17-28. (Year: 2018).*
PCT International Search Report and Written Opinion in International Application No. PCT/US2021/016660, dated May 5, 2021, 11 pages.

* cited by examiner

*Primary Examiner* — Paul J Holland
(74) *Attorney, Agent, or Firm* — DLA Piper LLP (US)

(57) ABSTRACT

The invention provides important tools for the use of Chlorophyte organisms, including regulatory sequences useful for the expression of transgenes in such organisms. Also provided are vectors and expression cassettes containing promoters and/or terminators disclosed herein for expression of transgenes in Chlorophyte organisms. Methods of using these tools are also provided.

24 Claims, No Drawings

Specification includes a Sequence Listing.

SEQUENCE LISTING

```
<160> NUMBER OF SEQ ID NOS: 20

<210> SEQ ID NO 1
<211> LENGTH: 245
<212> TYPE: DNA
<213> ORGANISM: Picochlorum sp.
<220> FEATURE:
<221> NAME/KEY: misc_feature
<223> OTHER INFORMATION: CP12 promoter

<400> SEQUENCE: 1
gtatctttga aaattctact catctgtgcg cccagatcta ttgcctcatc gtgatcagat      60
ctattcttaa ttccgatcag acgatattca aatgtttcaa acatggagtt ccgtacttta     120
aaaaaatctt ctcgcagcgc ctctgtggat aagacgacag aaaaccccat ccacagattt     180
acgaatttgc aatacaacgc accattaaac ccactaaatc aatcaatttt aaacaacaga     240
ttacg                                                                 245

<210> SEQ ID NO 2
<211> LENGTH: 432
<212> TYPE: DNA
<213> ORGANISM: Picochlorum sp.
<220> FEATURE:
<221> NAME/KEY: misc_feature
```

<223> OTHER INFORMATION: CP12 terminator

<400> SEQUENCE: 2

| | | | | | |
|---|---|---|---|---|---|
| ttcgctctct | ggagcactgc | agtagcataa | ttcatataga | tgatgcaagc | atgtgattat | 60 |
| gtttcgttgt | cgtatgtata | caaagcaaag | catgtaacat | tggttgacat | cactacccat | 120 |
| cttgatgatg | tgcaacaaga | catctttcca | atgcaagatt | acatgcgctc | atcattaaaa | 180 |
| tatctacgag | aaaaaaaggt | acatgtgtac | tctcaaatgg | acatcatagt | atgtagtttt | 240 |
| gtaagatgca | gattttcttt | caccgatgga | aggatgcagt | gctgcaagtc | acaagtgtca | 300 |
| gaccatctat | tatgcagtgt | aaataccaag | aatgctgcag | tacttggtat | agaaaaaaaa | 360 |
| catgtgtata | gatcgacaat | gatccaatat | aaacaggtga | attcagcctc | tgaataaagg | 420 |
| aattccatat | ca | | | | | 432 |

<210> SEQ ID NO 3
<211> LENGTH: 931
<212> TYPE: DNA
<213> ORGANISM: Picochlorum sp.
<220> FEATURE:
<221> NAME/KEY: misc_feature
<223> OTHER INFORMATION: CPP1 promoter

<400> SEQUENCE: 3

| | | | | | |
|---|---|---|---|---|---|
| atcactagtg | aataaatgtg | atgtactctt | gcacgattgc | acatatagcg | tgcattgtgc | 60 |
| gataagaatg | gccagtatcc | aacaatactt | gttggcctgg | agtcgcccct | gcacacacgc | 120 |
| aagtcgttaa | cgcactcatc | catcattgcc | ctttttccgc | tgtaattttg | cgtactacct | 180 |
| accatatcac | acttttagaa | ctcttatagc | aaaggtaacg | gcgtaaataa | tggtctataa | 240 |
| ctattctttg | gctttctagg | ttgtgggcga | tctctctggg | aagttgttca | cccaagtacc | 300 |
| tgcgacgtcg | gaacaatggc | tttaaatccc | acaaagctcg | aatatgttta | gtaaagagat | 360 |
| gatcttggtg | gttgattaca | gcgccatgga | gactatgggg | gacgatgcgc | cattcacgcg | 420 |
| tcgttgctca | acacctaggt | gtgcactgct | cttgtctccg | gtcgacgggg | ttgtattgta | 480 |
| ggaaggcttg | ttacgagccc | atcggaagtt | cccgctgtca | gggactccct | ggacaggacc | 540 |
| cgttccaatg | ctactgatcc | aatctactac | gcattgatgc | tcagaaaggg | tgtcgaacta | 600 |
| tctgtggtgt | ccattgcggc | attgaaacga | tcggtttgta | aatcctaggc | aagatacgtt | 660 |
| gcatggggat | gagggggtcgg | agttccaagg | agctgatgca | cccatcgtca | cacctgtcag | 720 |
| agcccttgtt | tgaccggcca | gagatatcaa | tgtcgatctt | ccgttgttta | cagttcgttg | 780 |
| gaccaatata | atcagttggg | tacaaattcc | gtggattctg | acactctgcg | acacaaaaat | 840 |
| tttacttgaa | tactatcaac | cgcccacaag | tgttgatcat | tcatacagtt | cattggaact | 900 |
| tgtgcattc | agacaaacaa | aagagaaaga | a | | | 931 |

<210> SEQ ID NO 4
<211> LENGTH: 377
<212> TYPE: DNA
<213> ORGANISM: Picochlorum sp.
<220> FEATURE:
<221> NAME/KEY: misc_feature
<223> OTHER INFORMATION: CPP1 terminator

<400> SEQUENCE: 4

| | | | | | |
|---|---|---|---|---|---|
| aggcgacaaa | agcaaatgcc | acttgacaca | cgttaagcag | cgttgattgt | agcctgatac | 60 |
| atacaaatac | gaaaatcaaa | tagtgtgcta | ttttggcaag | atttgtgcat | atatttcatc | 120 |
| atggagattt | ctttatttca | ttcaatgtaa | tgtgttcgat | caattcaatc | tttctgagag | 180 |

```
agtaaagttc aatatcatgg tttcagaatg tccttggggc tgtaaaagct gggactgctg    240
tattgcaact gctacgtttg ctgtgaagaa atcttccaca tgtttcttca gagaccaatt    300
tttactcaga gggcatgcaa tgtatacatg tgttccatg gtacctaaac gagaaatatc    360
atcaactatt tgtatcg                                                    377
```

<210> SEQ ID NO 5
<211> LENGTH: 323
<212> TYPE: DNA
<213> ORGANISM: Picochlorum sp.
<220> FEATURE:
<221> NAME/KEY: misc_feature
<223> OTHER INFORMATION: FDX1 promoter

<400> SEQUENCE: 5

```
tcgagaagac aggcccatgt cttgcactgt gggagcagca tccttcacta tcaaaggccc     60
taggcgatgg gaatcaacgg gcgagcattc atcggtccca tgctcccaat cattcctaac   120
ggtcgacggt atgacgcagc caccctggtg ggtatacccca tcatcaccag acagtccgat   180
cgagagatgc ggcagaccgt tagaaaagga gcaaatgctg agtcgacccc aatctgaaga   240
taaggcgtcc agaacctcct ggccacgcac tcttaatatc ccaattttga ccaatcgaat   300
acgtacattt tcattaaatc aca                                           323
```

<210> SEQ ID NO 6
<211> LENGTH: 289
<212> TYPE: DNA
<213> ORGANISM: Picochlorum sp.
<220> FEATURE:
<221> NAME/KEY: misc_feature
<223> OTHER INFORMATION: FDX1 terminator

<400> SEQUENCE: 6

```
gcagctgagg ctttggtgac aaggatgaat cttttcacatg tgtgcagttg taattgttgg    60
gcagatcatc tcacattgct gtgtatttga taatatccat ctttcattac aattgtaaac   120
atatcatagt ccatgttata ttcttttttt ttcagaaatg gctttcaatc atcaagctca   180
tcatcaatga caacatcctc cccatcctca atatcctctg cttccatact agattcccgg   240
atctgttgct cgacgttata gactacatct agtatacttt tgaattgcg               289
```

<210> SEQ ID NO 7
<211> LENGTH: 250
<212> TYPE: DNA
<213> ORGANISM: Picochlorum sp.
<220> FEATURE:
<221> NAME/KEY: misc_feature
<223> OTHER INFORMATION: RBCS1 promoter

<400> SEQUENCE: 7

```
gtcgttacaa cacactcgct ctttctacca atgcaatgat ggcgactctg atgatgagag    60
caaatggaac caaggaccag gacattcgat cctggtatcc ttggagaaaa gaaagtcaga   120
atacaatgtc atcaccgccg atggataaga cggcattgcc actctagaag agccctcaca   180
tttaatacta atcgatctaa aacttgtgct tggcccgcac ctgtcgtcaa tttaattctc   240
aagaatcaaa                                                          250
```

<210> SEQ ID NO 8
<211> LENGTH: 392
<212> TYPE: DNA
<213> ORGANISM: Picochlorum sp.

```
<220> FEATURE:
<221> NAME/KEY: misc_feature
<223> OTHER INFORMATION: RBCS1 terminator

<400> SEQUENCE: 8
gctggtgaga gtgttgcttg atttgagtgc taaagattct actaccaagc tgaattcttt      60
agtgaggtga tcattcaatc tggatcccat gattgtgtca tcaactcagg tctgagatga     120
aaaaaacctg tccgggagag ttgcatgtgg ttggacattt tcatgttttg tatgttcgga     180
agaattttct caatcaacat attttgtca tatctctctg tatgtaacat actcttgggc      240
attggaacta ttgtattcac acacttgagt gtcaacaatg tgtgtacgtt aagctgcttg     300
agtcagagct gcaaatctgc aataagaggc aattgttccg caaagagcat cttattcgta     360
ggccaactcg catccttcca aacagttatt tc                                   392

<210> SEQ ID NO 9
<211> LENGTH: 483
<212> TYPE: DNA
<213> ORGANISM: Picochlorum sp.
<220> FEATURE:
<221> NAME/KEY: misc_feature
<223> OTHER INFORMATION: LHCII promoter

<400> SEQUENCE: 9
tccaaccatc caaagcccag acgagattca actcatgtac acaccaccat gtctcagacc      60
tggagcagtc ggctggttcc cagagcaggg taagatttgg gaaaagtacg gtctcccgaa     120
attccttgga cctgatcctt caaagaagct gaacaagcaa gataccaaga agacatgta      180 aatcagacca tatcgaaatc aagattgatt gatgaccccg gggacaaaag gacccgaaac     240
cacatcaaga taaccaaaga tttttttccta tcggcgatat atcacaagat atcccatcaa    300
agggtcgatt tgatgggacc atagtgtcat tcttcgtgtc atccaaggcc atccttttcg     360
ggaatcaatg tccacgaaaa tctatgctga tgatcaagac aggatctgcc caaccccggt     420
acttttaatt ctcgataatt tcatttccag tcaaatttcg acgatctatt caaacaaatc    480
aag                                                                   483

<210> SEQ ID NO 10
<211> LENGTH: 484
<212> TYPE: DNA
<213> ORGANISM: Picochlorum sp.
<220> FEATURE:
<221> NAME/KEY: misc_feature
<223> OTHER INFORMATION: Pico LHCII terminator

<400> SEQUENCE: 10
taagtgtata gtttccttga atatccttca ggggatgcca catggtaatg tttcattgtg      60
atgtggttgc atgacaaaca ggtgtcatca tctcttgaag cgtaaaaaaa tggatgcagt     120
ttgagcaccc ttgtatattt ttttcccaa aaatatttgt gtaacaaaac gcatccatag     180
ctgtgagcta gtagtagttt tacaaatgaa aagaatcatt cattatgata catgattatt     240
attcctcaca gtacacgcac tcattattga aaattcgtcg ctttattccg tatttataca     300
tctagagttc tgttcacgac taactagact gctcagttga gcgagctcgg agatccaggg    360
ctgcgttgca tatggatatc tggtgtttcg aatgaatttg acgatataat atcaaacagt    420
ccatctggat tatccgcatg cacccagtgg accgctgttt cgtaacaaat gaacccgatg    480
ccca                                                                  484
```

<210> SEQ ID NO 11
<211> LENGTH: 346
<212> TYPE: DNA
<213> ORGANISM: Picochlorum sp.
<220> FEATURE:
<221> NAME/KEY: misc_feature
<223> OTHER INFORMATION: NAR promoter

<400> SEQUENCE: 11

```
ttgcctatac agtatcgatg gatgcgttgt cattttcaaa aagatacatc tttaagaata    60
tcagcaacca tatgggcctg ctcttgtatc aaatggataa gaggaagcat gatcaaagtc   120
cagacctact actcctaccc tggctcacga ggagattcag tttgagtctg agtccactga   180
ctcacataca tcagggtttt ccatgaacga tgaacagatg gaaggcgttg ctgataatct   240
aatttcacat ttaattacat ttcatgattt taaaacaca tcagttgtag tcttttggcc   300
tcaatctcac tgtgggattt ttcaactggg tgatactgtc ttcaag                  346
```

<210> SEQ ID NO 12
<211> LENGTH: 929
<212> TYPE: DNA
<213> ORGANISM: Picochlorum sp.
<220> FEATURE:
<221> NAME/KEY: misc_feature
<223> OTHER INFORMATION: NAR terminator

<400> SEQUENCE: 12

```
gttcttgcat ggccttttga ttgctgattt aatgaaagtt tacattccat ttaataattc    60
atagcgcccg tgtgtgtcaa ataaaatcaa agcattacaa aatctctaca ttcaaaaccg   120
tttgaatggc cttgtctcat gaaaacataa tccaatcaaa gcgaagaata accaggcagt   180
aaacttatac tccttgcttg aatcttcctt ttggtatgtc acaatggaac caatgcatgc   240
aaccaacccc atcaagaatc caacacaata cctaaactgt agccaaggag ttgtcagctc   300
ctgccaaact gtacgcttat tcttattact ctgtactgac ggttctttcg gttgttgctc   360
tacacccttc ctgcttttcc gccgtctcag ctctacagca gcaccagtct tggcagagga   420
cctagcttca ggcatactca atacgttttc cacagaaatc tccgtttctt cgagaatggg   480
cgtaaatatc gtcaatatta aattcgaaca aaaattaacg ctgcaagtac agtgaaattc   540
aaaatataga ttcaatctgc ccaaaccaaa cctagggcac ggtcatatga cgcaacccag   600
actcaattgc aattctgagt ctgcagactc tcattcatt catcatggat ccgattgagc   660
tttgacaccc atgatggtgg atggacgata tctcatactc gctcttattc tcatgtatgt   720
atcgcatcgg atgaattgac tgtgccagcc tggagaagaa gaagtcttgg accaatgcat   780
tattactgca ccattaccag gccttggaaa gatccacaga gacttgtgca tatgattgat   840
tacaactcta gccttctagt gtacattata ttttaacatc gaaacgcaaa tttacatgaa   900
aaaaaatcgt tattgttact atcaaatca                                     929
```

<210> SEQ ID NO 13
<211> LENGTH: 1319
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BSD_PicoOpt2_CP12-PT, blasticidin vector with
      CP12 promoter and terminator

<400> SEQUENCE: 13

```
gtatctttga aaattctact catctgtgcg cccagatcta ttgcctcatc gtgatcagat      60
ctattcttaa ttccgatcag acgatattca aatgtttcaa acatggagtt ccgtacttta     120
aaaaaatctt ctcgcagcgc ctctgtggat aagacgacag aaacccccat ccacagattt     180
acgaatttgc aatacaacgc accattaaac ccactaaatc aatcaatttt aaacaacaga     240
ttacgatgcc actttctcaa gaggaatcta cactgatcga gagagcaaca gcaacgatca     300
atagcatccc aatctccgag gactactctg ttgcatcagc agcgttgtcg agcgatggaa     360
ggatctttac tggggtgaac gtgtatcact tcacggcgg accatggtac gtgttgatgg      420
ttcttcatcg agtcgagaac gttttttccat cgtagaggct ctagtaggcc cccaagacgc    480
catgctaaag ctatatcatg aagacataca tccatatttt tcaaatatgt gtgtccaagg    540
agcgatatgc atccgaggct tcgtcggaca gacagagatc tgtttgtcca caccttgact    600
gtgcaaacct agatggatac cctgctaacg tgcgatatgt gtatcatgat tgcagtgctg    660
aattggtggt gttgggaaca gcagcagcag cagcagcggg aaatcttaca tgtatagtgg    720
caatcgggaa cgagaatagg ggaatacttt ctccatgcgg aagatgtcga caagtgttgt    780
tggatctgca tccgggaatc aaggcaatcg tgaaggatag tgatggacag ccaacagcag    840
tgggaataag agaacttctg ccatctggat acgtgtggga aggatgattc gctctctgga    900
gcactgcagt agcataattc atatagatga tgcaagcatg tgattatgtt tcgttgtcgt    960
atgtatacaa agcaaagcat gtaacattgg ttgacatcac tacccatctt gatgatgtgc   1020
aacaagacat ctttccaatg caagattaca tgcgctcatc attaaaatat ctacgagaaa   1080
aaaaggtaca tgtgtactct caaatggaca tcatagtatg tagttttgta agatgcagat   1140
tttctttcac cgatggaagg atgcagtgct gcaagtcaca agtgtcagac catctattat   1200
gcagtgtaaa taccaagaat gctgcagtac ttggtataga aaaaaaacat gtgtatagat   1260
cgacaatgat ccaatataaa caggtgaatt cagcctctga ataaggaat tccatatca    1319
```

<210> SEQ ID NO 14
<211> LENGTH: 2041
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BSD_PicoOpt2_CPP1-PTI, blasticidin vector with CPP promoter and terminator

<400> SEQUENCE: 14

```
atcactagtg aataaatgtg atgtactctt gcacgattgc acatatagcg tgcattgtgc      60
gataagaatg ccagtatcc aacaatactt gttggcctgg agtcgcccct gcacacacgc     120
aagtcgttaa cgcactcatc catcattgcc cttttccgc tgtaattttg cgtactacct     180
accatatcac acttttagaa ctcttatagc aaaggtaacg gcgtaaataa tggtctataa    240
ctattctttg gctttctagg ttgtgggcga tctctctggg aagttgttca cccaagtacc    300
tgcgacgtcg gaacaatggc tttaaatccc acaaagctcg aatatgttta gtaaagagat    360
gatcttggtg gttgattaca gcgccatgga gactatgggg gacgatgcgc cattcacgcg    420
tcgttgctca acacctaggt gtgcactgct cttgtctccg gtcgacgggg ttgtattgta    480
ggaaggcttg ttacgagccc atcggaagtt cccgctgtca gggactccct ggacaggacc    540
cgttccaatg ctactgatcc aatctactac gcattgatgc tcagaaaggg tgtcgaacta    600
tctgtggtgt ccattgcggc attgaaacga tcggtttgta aatcctaggc aagatacgtt    660
```

```
gcatggggat gaggggtcgg agttccaagg agctgatgca cccatcgtca cacctgtcag    720
agcccttgtt tgaccggcca gagatatcaa tgtcgatctt ccgttgttta cagttcgttg    780
gaccaatata atcagttggg tacaaattcc gtggattctg acactctgcg acacaaaaat    840
tttacttgaa tactatcaac cgcccacaag tgttgatcat tcatacagtt cattggaact    900
ttgtgcattc agacaaacaa aagagaaaga aatgccactt tctcaagagg aatctacact    960
gatcgagaga gcaacagcaa cgatcaatag catcccaatc tccgaggact actctgttgc   1020
atcagcagcg ttgtcgagcg atggcaggta tgttatagaa tcatgggaaa tcggtattat   1080
gtctagattc gggggatatg tgtgatatgg cacgagctcg gctgctgtac ccatcatggg   1140
tggtggtgtg ctgcatggag tcatctccgc ccatcttcgt gctgatccag ttgttttcaa   1200
cctagaaaca gccatccttg acatattata catctatatg atatgaagta caagtttggg   1260
ctggtttcac ggtggcatcg ggggatcgaa gtttggttga ttaccccatg ctggccaact   1320
ggcaacacaa aacctcatct gttgctattt ttcagtctca ttaaccttttt gatttgtatc   1380 tctacaggat ctttactggg gtgaacgtgt atcacttcac gggcggacca tgtgctgaat   1440
tggtggtgtt gggaacagca gcagcagcag cagcgggaaa tcttacatgt atagtggcaa   1500
tcgggaacga gaataggtga atactttctc catgcggaag atgtcgacaa gtgttgttgg   1560
atctgcatcc gggaatcaag gcaatcgtga aggatagtga tggacagcca acagcagtgg   1620
gaataagaga acttctgcca tctggatacg tgtgggaagg atgaaggcga caaaagcaaa   1680
tgccacttga cacacgttaa gcagcgttga ttgtagcctg atacatacaa atacgaaaat   1740
caaatagtgt gctattttgg caagatttgt gcatatattt catcatggag atttctttat   1800
ttcattcaat gtaatgtgtt cgatcaattc aatctttctg agagagtaaa gttcaatatc   1860
atggtttcag aatgtccttg gggctgtaaa agctgggact gctgtattgc aactgctacg   1920
tttgctgtga agaaatcttc cacatgtttc ttcagagacc aattttttact cagagggcat   1980 gcaatgtata catgtgtttc catggtacct aaacgagaaa tatcatcaac tatttgtatc   2040
g                                                                   2041
```

<210> SEQ ID NO 15  
<211> LENGTH: 1331  
<212> TYPE: DNA  
<213> ORGANISM: Artificial Sequence  
<220> FEATURE:  
<223> OTHER INFORMATION: Synthetic  
<220> FEATURE:  
<221> NAME/KEY: misc_feature  
<223> OTHER INFORMATION: BSD_PicoOpt2_FDX1-PTI, blasticidin vector with ferrodoxin promoter and terminator

<400> SEQUENCE: 15

```
tcgagaagac aggcccatgt cttgcactgt gggagcagca tccttcacta tcaaaggccc     60
taggcgatgg gaatcaacgg gcgagcattc atcggtccca tgctcccaat cattcctaac    120
ggtcgacggt atgacgcagc caccctggtg ggtataccca tcatcaccag acagtccgat    180
cgagagatgc ggcagaccgt tagaaaagga gcaaatgctg agtcgacccc aatctgaaga    240
taaggcgtcc agaacctcct ggccacgcac tcttaatatc ccaattttga ccaatcgaat    300
acgtacattt tcattaaatc acaatgccac tttctcaaga ggaatctaca ctgatcgaga    360
gagcaacagc aacgatcaat agcatcccaa tctccgagga ctactctgtt gcatcagcag    420
cgttgtcgag cgatggaagg atctttacag gtacgccgat gcttgatgat gctggcgtct    480
```

```
gaactttaca gggtggagcg atgggcttga tgtcgcctct aatatgttct atatatatca    540
ttgataataa tgtgatggtc cactgatgca atacatcatg tatcgttgca ggcgtgaacg    600
tgtatcactt cacgggcgga ccatgtgctg aattggtggt gttgggaaca gcagcagcag    660
cagcagcagg tatgtttgga ttttgcgtgg gatgagagat cgcgaccggt tgtgaggtcg    720
tggtgccagg tcatgtagta gtcttggtcc ttgctgtttg aggatgggcc tcactgctgg    780
cctacctggg cacccatgt cagcaaatcg tatatggcca cgtataacga tgtgcacctc    840
tttttcttat gcaggaaatc ttacatgtat agtggcaatc gggaacgaga ataggggaat    900
actttctcca tgcggaagat gtcgacaagt gttgttggat ctgcatccgg aatcaaggc    960
aatcgtgaag atagtgatg acagccaac agcagtggga ataagagaac ttctgccatc    1020
tggatacgtg tgggaaggat gagcagctga ggctttggtg acaaggatga atctttcaca    1080
tgtgtgcagt tgtaattgtt gggcagatca tctcacattg ctgtgtattt gataatatcc    1140
atctttcatt acaattgtaa acatatcata gtccatgtta tattctttttt ttttcagaaa   1200
tggctttcaa tcatcaagct catcatcaat gacaacatcc tccccatcct caatatcctc    1260
tgcttccata ctagattccc ggatctgttg ctcgacgtta tagactacat ctagtatact    1320
tttgaattgc g                                                         1331

<210> SEQ ID NO 16
<211> LENGTH: 1353
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: BSD_PicoOpt2_RBCS1-PTI, blasticidin vector with
      rubisco promoter and terminator

<400> SEQUENCE: 16
gtcgttacaa cacactcgct ctttctacca atgcaatgat ggcgactctg atgatgagag     60
caaatggaac caaggaccag gacattcgat cctggtatcc ttggagaaaa gaaagtcaga    120
atacaatgtc atcaccgccg atggataaga cggcattgcc actctagaag agccctcaca    180
tttaatacta atcgatctaa aacttgtgct tggcccgcac ctgtcgtcaa tttaattctc    240
aagaatcaaa atgccacttt ctcaagagga atctacactg atcgagagag caacagcaac    300
gatcaatagc atcccaatct ccgaggacta ctctgttgca tcagcagcgt tgtcgagcga    360
tggaaggatc tttactgggg tgaacgtgta tcacttcaca ggtgagttat tgttgtttga    420
tcgtgaatgt agcaggccaa tgggcgtcat gagcgtccat ggagtcgatg gataaggagg    480
gccgccttca acttcctact acgctctcga tgaccgattt tgtcctcttc gagtcgtcat    540
ctagcgcgga tatgtgatca ataatagtta ttgactataa tggataacac attgtggcga    600
tcgtcacgga tgcggcgaga acatcacatc ggggaagaga gcgttttgac ctaggcagtg    660
atatggcgta ctcgcgttgt ggtgatcctg tctgacctaa acaactaatc atcatgcagg    720
tggaccatgt gctgaattgg tggtgttggg aacagcagca gcagcagcag cgggaaatct    780
tacatgtata gtggcaatcg ggaacgagaa taggggaata cttctccat gcggaagatg    840
tcgacaagtg ttgttggatc tgcatccggg aatcaaggca atcgtgaagg atagtgatgg    900
acagccaaca gcagtgggaa taagagaact tctgccatct ggatacgtgt gggaaggatg    960
agctggtgag agtgttgctt gatttgagtg ctaaagattc tactaccaag ctgaattctt   1020
tagtgaggtg atcattcaat ctggatccca tgattgtgtc atcaactcag gtctgagatg   1080
```

```
aaaaaaacct gtccgggaga gttgcatgtg gttggacatt ttcatgtttt gtatgttcgg    1140
aagaattttc tcaatcaaca tattttttgtc atatctctct gtatgtaaca tactcttggg    1200
cattggaact attgtattca cacacttgag tgtcaacaat gtgtgtacgt taagctgctt    1260
gagtcagagc tgcaaatctg caataagagg caattgttcc gcaaagagca tcttattcgt    1320
aggccaactc gcatccttcc aaacagttat ttc                                  1353
```

<210> SEQ ID NO 17
<211> LENGTH: 1052
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ZeoR_PicoOpt2_CP12-PT, zeocin vector with CP12
    promoter and terminator

<400> SEQUENCE: 17

```
gtatctttga aaattctact catctgtgcg cccagatcta ttgcctcatc gtgatcagat     60
ctattcttaa ttccgatcag acgatattca aatgtttcaa acatggagtt ccgtactttta    120 aaaaaatctt ctcgcagcgc ctctgtggat aagacgacag aaaaccccat ccacagattt    180
acgaatttgc aatacaacgc accattaaac ccactaaatc aatcaatttt aaacaacaga    240
ttacgatggc caagttgaca tctgctgttc cagtgttaac ggcaagagat gttgctggag    300
cagtggagtt ttggaccgat agactggggt ttagtcgcga ctttgtggaa gatgactttg    360
ctggagtggt gagagatgat gtgacactgt tcatcagcgc agtccaagat caagttgtgc    420
cggataatac actggcatgg gtttgggtta gagggttaga tgagctctat gctgagtggt    480
ctgaagttgt gtccacgaac tttcgggatg catctggacc agcaatgaca gaaatcggag    540
aacaaccatg gggaagggag tttgctttga gagatccagc tggaaactgc gttcactttg    600
tggctgaaga gcaggactag ttcgctctct ggagcactgc agtagcataa ttcatataga    660
tgatgcaagc atgtgattat gtttcgttgt cgtatgtata caaagcaaag catgtaacat    720
tggttgacat cactacccat cttgatgatg tgcaacaaga catctttcca atgcaagatt    780
acatgcgctc atcattaaaa tatctacgag aaaaaaaggt acatgtgtac tctcaaatgg    840
acatcatagt atgtagtttt gtaagatgca gattttctttt caccgatgga aggatgcagt    900
gctgcaagtc acaagtgtca gaccatctat tatgcagtgt aaataccaag aatgctgcag    960
tacttggtat agaaaaaaaa catgtgtata gatcgacaat gatccaatat aaacaggtga    1020
attcagcctc tgaataaagg aattccatat ca                                   1052
```

<210> SEQ ID NO 18
<211> LENGTH: 1301
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ZeoR_PicoOpt2_CP12-PTI, zeocin vector with CP12
    promoter and terminator

<400> SEQUENCE: 18

```
gtatctttga aaattctact catctgtgcg cccagatcta ttgcctcatc gtgatcagat     60
ctattcttaa ttccgatcag acgatattca aatgtttcaa acatggagtt ccgtactttta    120
```

| | |
|---|---|
| aaaaaatctt ctcgcagcgc ctctgtggat aagacgacag aaaaccccat ccacagattt | 180 |
| acgaatttgc aatacaacgc accattaaac ccactaaatc aatcaatttt aaacaacaga | 240 |
| ttacgatggc aagttgaca tctgctgttc cagtgttaac ggcaagagat gttgctggag | 300 |
| cagtggagtt ttggaccgat agactgggt ttagtcgcga ctttgtggaa gatgactttg | 360 |
| ctggagtggt gagagatgat ggtacgtgtt gatggttctt catcgagtcg agaacgtttt | 420 |
| tccatcgtag aggctctagt aggcccccaa gacgccatgc taaagctata tcatgaagac | 480 |
| atacatccat attttttcaaa tatgtgtgtc caaggagcga tatgcatccg aggcttcgtc | 540 |
| ggacagacag agatctgttt gtccacacct tgactgtgca aacctagatg datccctgc | 600 |
| taacgtgcga tatgtgtatc atgattgcag tgacactgtt catcagcgca gtccaagatc | 660 |
| aagttgtgcc ggataataca ctggcatggg tttgggttag agggttagat gagctctatg | 720 |
| ctgagtggtc tgaagttgtg tccacgaact ttcgggatgc atctggacca gcaatgacag | 780 |
| aaatcggaga caaccatgg ggaagggagt ttgctttgag agatccagct ggaaactgcg | 840 |
| ttcactttgt ggctgaagag caggactagt tcgctctctg gagcactgca gtagcataat | 900 |
| tcatatagat gatgcaagca tgtgattatg tttcgttgtc gtatgtatac aaagcaaagc | 960 |
| atgtaacatt ggttgacatc actacccatc ttgatgatgt gcaacaagac atctttccaa | 1020 |
| tgcaagatta catgcgctca tcattaaaat atctacgaga aaaaaggta catgtgtact | 1080 |
| ctcaaatgga catcatagta tgtagttttg taagatgcag attttctttc accgatggaa | 1140 |
| ggatgcagtg ctgcaagtca caagtgtcag accatctatt atgcagtgta aataccaaga | 1200 |
| atgctgcagt acttggtata gaaaaaaaac atgtgtatag atcgacaatg atccaatata | 1260 |
| aacaggtgaa ttcagcctct gaataaagga attccatatc a | 1301 |

<210> SEQ ID NO 19
<211> LENGTH: 1313
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ZeoR_PicoOpt2_FDX1-PTI, zeocin vector with ferredoxin promoter and terminator

<400> SEQUENCE: 19

| | |
|---|---|
| tcgagaagac aggcccatgt cttgcactgt gggagcagca tccttcacta tcaaaggccc | 60 |
| taggcgatgg gaatcaacgg gcgagcattc atcggtccca tgctcccaat cattcctaac | 120 |
| ggtcgacggt atgacgcagc caccctggtg ggtatacca tcatcaccag acagtccgat | 180 |
| cgagagatgc ggcagaccgt tagaaaagga gcaaatgctg agtcgacccc aatctgaaga | 240 |
| taaggcgtcc agaacctcct ggccacgcac tcttaatatc ccaattttga ccaatcgaat | 300 |
| acgtacattt tcattaaatc acaatggcca agttgcatc tgctgttcca gtgttaacgg | 360 |
| caagagatgt tgcaggtacg ccgatgcttg atgatgctgg cgtctgaact ttacagggtg | 420 |
| gagcgatggg cttgatgtcg cctctaatat gttctatata tatcattgat aataatgtga | 480 |
| tggtccactg atgcaataca tcatgtatcg ttgcaggcgc agtggagttt tggaccgata | 540 |
| gactggggtt tagtcgcgac tttgtggaag atgactttgc tggagtggtg agagatgatg | 600 |
| tgacactgtt catcagcgca gtccaggtat gtttggattt tgcgtgggat gagagatcgc | 660 |
| gaccggttgt gaggtcgtgg tgccaggtca tgtagtagtc ttggtccttg ctgtttgagg | 720 |
| atgggcctca ctgctggcct acctgggcac cccatgtcag caaatcgtat atggccacgt | 780 |

```
ataacgatgt gcacctcttt ttcttatgca ggatcaagtt gtgccggata atacactggc    840
atgggtttgg gttagagggt tagatgagct ctatgctgag tggtctgaag ttgtgtccac    900
gaactttcgg gatgcatctg gaccagcaat gacagaaatc ggagaacaac catggggaag    960
ggagtttgct ttgagagatc cagctggaaa ctgcgttcac tttgtggctg aagagcagga   1020
ctaggcagct gaggctttgg tgacaaggat gaatctttca catgtgtgca gttgtaattg   1080
ttgggcagat catctcacat tgctgtgtat ttgataatat ccatctttca ttacaattgt   1140
aaacatatca tagtccatgt tatattcttt tttttcaga  aatggctttc aatcatcaag   1200
ctcatcatca atgacaacat cctccccatc ctcaatatcc tctgcttcca tactagattc   1260
ccggatctgt tgctcgacgt tatagactac atctagtata cttttgaatt gcg          1313
```

```
<210> SEQ ID NO 20
<211> LENGTH: 1017
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ZeoR_PicoOpt2_RBCS1-PT, zeocin vector with
      rubisco promoter and terminator

<400> SEQUENCE: 20
gtcgttacaa cacactcgct ctttctacca atgcaatgat ggcgactctg atgatgagag     60
caaatggaac caaggaccag gacattcgat cctggtatcc ttggagaaaa gaaagtcaga    120
atacaatgtc atcaccgccg atggataaga cggcattgcc actctagaag agccctcaca    180
tttaatacta atcgatctaa aacttgtgct tggcccgcac ctgtcgtcaa tttaattctc    240
aagaatcaaa atggccaagt tgacatctgc tgttccagtg ttaacggcaa gagatgttgc    300
tggagcagtg gagttttgga ccgatagact ggggtttagt cgcgactttg tggaagatga    360
ctttgctgga gtggtgagag atgatgtgac actgttcatc agcgcagtcc aagatcaagt    420
tgtgccggat aatacactgg catgggtttg ggttagaggg ttagatgagc tctatgctga    480
gtggtctgaa gttgtgtcca cgaactttcg ggatgcatct ggaccagcaa tgacagaaat    540
cggagaacaa ccatggggaa gggagtttgc tttgagagat ccagctggaa actgcgttca    600
ctttgtggct gaagagcagg actaggctgg tgagagtgtt gcttgatttg agtgctaaag    660
attctactac caagctgaat tctttagtga ggtgatcatt caatctggat cccatgattg    720
tgtcatcaac tcaggtctga gatgaaaaaa acctgtccgg gagagttgca tgtggttgga    780
cattttcatg ttttgtatgt tcggaagaat tttctcaatc aacatatttt tgtcatatct    840
ctctgtatgt aacatactct tgggcattgg aactattgta ttcacacact tgagtgtcaa    900
caatgtgtgt acgttaagct gcttgagtca gagctgcaaa tctgcaataa gaggcaattg    960
ttccgcaaag agcatcttat tcgtaggcca actcgcatcc ttccaaacag ttatttc      1017
```

REGULATORY SEQUENCES FOR EXPRESSION OF TRANSGENES

CROSS-REFERENCE TO RELATED APPLICATIONS

This application claims benefit of priority under 35 U.S.C. § 119(e) of U.S. Ser. No. 62/970,580, filed Feb. 5, 2020, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2250_1_Sequence_Listing, was created on Jan. 20, 2021, and is 25 kb. The file can be accessed using Microsoft Word on a computer that uses Windows OS.

FIELD OF THE INVENTION

The invention involves the expression of transgenes in photosynthetic organisms using regulatory sequences.

BACKGROUND OF THE INVENTION

Algal cells are a promising source of biofuels. Their ability to harness solar energy to convert carbon dioxide into carbon-rich lipids already exceeds the abilities of oil-producing agricultural crops, with the added advantage that algae grown for biofuel do not compete with oil-producing crops for agricultural land. Green algae of the phylum Chlorophyta and Trebouxiophyceae class can be cultured easily, rapidly, and economically. In order to maximize algal fuel production, new and engineered algal strains are needed for growth and carbon fixation at an industrial scale. The manipulation of algal genomes has proven difficult to date because of the thick cell wall that surrounds many algal cells. Consistent procedures for genetic manipulation of these organisms are needed. Furthermore, modern recombinant strain development requires robust and efficient tools for expressing transgenes to alter cellular metabolism and physiology in desired ways. An essential component of any genetic engineering "toolkit" is a suite of functional regulatory sequences to drive transgene-expression. There is a need for endogenous promoters, cloned and verified, from the strains for which recombinant DNA technology is being developed as well as additional strategies for increasing transformation of microorganisms such as algae and improved expression of heterologous genes.

SUMMARY OF THE INVENTION

The invention provides important tools for use in algal host cells or organisms, including regulatory and control sequences useful for the expression of transgenes in such host cells or organisms. Also provided are vectors and expression cassettes containing promoters and/or terminators disclosed herein for expression of transgenes in algal host cells or organisms. Methods of using these tools are also provided.

In a first aspect the invention provides a nucleic acid sequence comprising a promoter having at least 75% sequence identity to a sequence selected from the group consisting of: SEQ ID NO: 1, 3, 5, 7, 9, and 11, and operably linked to a heterologous sequence of interest. In one embodiment the nucleic acid sequence is comprised in a vector for transforming a microorganism. Any of the nucleic acid sequences disclosed herein can be contained in a microorganism. The microorganism can be an algal microorganism that expresses the heterologous sequence of interest. For example, the algal microorganism can be a Chlorophyte microorganism, and can be of the Class Trebouxiophyceae. In some embodiments the nucleic acid sequence can also have a terminator sequence, and can also be comprised in an expression cassette. The terminator sequence can have at least 75% sequence identity to a terminator sequence within any one of SEQ ID NO: 2, 4, 6, 8, 10, and 12.

In one embodiment the nucleic acid sequence can be a promoter sequence having at least 75% sequence identity to a promoter sequence within SEQ ID NO: 1 and the terminator sequence can have at least 75% sequence identity to a terminator sequence within SEQ ID NO: 2; or the promoter can be a sequence having at least 75% sequence identity to a promoter sequence within SEQ ID NO: 3 and the terminator sequence can have at least 75% sequence identity to a terminator sequence within SEQ ID NO: 4; or the promoter sequence can have at least 75% sequence identity to a promoter sequence within SEQ ID NO: 5 and the terminator sequence can have at least 75% sequence identity to a terminator sequence within SEQ ID NO: 6; or the promoter sequence can have at least 75% sequence identity to a promoter sequence within SEQ ID NO: 7 and the terminator sequence can have at least 75% sequence identity to a terminator sequence within SEQ ID NO: 8.

In other embodiments the nucleic acid sequence can have a promoter sequence having at least 75% sequence identity to a promoter sequence within SEQ ID NO: 9 and the terminator sequence can have at least 75% sequence identity to a terminator sequence within SEQ ID NO: 10; or the promoter sequence can have at least 75% sequence identity to a promoter sequence within SEQ ID NO: 11 and the terminator sequence can have at least 75% sequence identity to a terminator sequence within SEQ ID NO: 12. Any of the nucleic acid sequences can be contained in a vector for transforming a microorganism. Any of the nucleic acid sequences having a promoter sequence disclosed herein can also have a terminator sequence disclosed herein. Any of the nucleic acid sequences disclosed herein can be contained in an expression cassette.

In another aspect the invention provides a method of transforming an algal cell involving introducing a vector having any expression cassette disclosed herein into an algal cell and selecting for a transformant.

In some embodiments the heterologous sequence of interest encodes a polypeptide or functional RNA. And in any of the embodiments the nucleic acid sequence of the invention can be operably linked to a nucleic acid sequence encoding a protein or functional RNA heterologous to *Picochlorum* sp.

DETAILED DESCRIPTION OF THE INVENTION

The present invention provides nucleic acid sequences and methods useful for the expression of transgenes in algal host organisms. The nucleic acid sequences can be regulatory sequences and control, e.g. promoters and/or terminators for expression of transgenes in the host organisms of the invention. The promoters and/or terminators can be useful for expressing, over-expressing, or under-expressing an exogenous or heterologous protein in the host organism.

The host cell or organism useful in the invention can be any eukaryotic microoalga such as, but not limited to, a Chlorophyte, an Ochrophyte, or a Charophyte alga. In some embodiments the algal host cell or organism can be a Chlorophyte alga of the taxonomic Class Chlorophyceace, or of the Class Chlorodendrophyceace, or the Class Prasinophyceace, or the Class Trebouxiophyceae, or the Class Eustigmatophyceae. In some embodiments, the algal host cell or organism can be a member of the Class Chlorophyceace, such as a species of any one or more of the genera *Asteromonas, Ankistrodesmus, Carteria, Chlamydomonas, Chlorococcum, Chlorogonium, Chlorodendrales, Chlorella, Chrysosphaera, Dunaliella, Haematococcus, Monoraphidium, Neochloris, Oedogonium, Pelagomonas, Pleurococcus, Pyrobotrys, Scenedesmus,* or *Volvox.* In other embodiments, the algal host cell or organism can be a member of the Class Chlorodendrophyceae, such as a species of any one or more of the genera *Prasinocladus, Scherffelia,* or *Tetraselmis.* In further alternative embodiments, the algal host cell or organism can be a member of the Class Prasinophyceace, optionally a species of any one or more of the genera *Ostreococcus* or *Micromonas.* Further alternatively, the algal host cell or organism can be a member of the Class Trebouxiophyceae, and optionally of the Order Chlorellales, and optionally a species of a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella,* or any of all possible combinations or sub-combination of the genera. In another embodiment the algal host cell or organism is a Chlorophyte alga of the Class Trebouxiophyceae, the Order Chlorellales, the Family selected from any of Oocystaceae, Chlorellaceae, or Eustigmatophyceae, and optionally a genera selected from one or more of *Oocystis, Parachlorella, Picochlorum, Nannochloropsis,* and *Tetraselmis.* In one embodiment the algal host cell or organism is of the Class Trebouxiophyceae and genus *Picochlorum.* In one embodiment the algal host cell or organism can also be from the genus Oocystis, or the genus *Parachlorella,* or the genus *Tetraselmis,* or from any of all possible combinations and sub-combinations of the genera. In one embodiment the host cell is *Picochlorum* sp.

The invention provides nucleic acid sequences encoding promoters and/or terminators. In any embodiment the nucleic acid sequences can be comprised in a vector for transforming a host cell or organism. In various embodiments the promoters can have a sequence selected from any promoter sequence of SEQ ID NO: 1-20 (e.g. 1, 3, 5, 7, 9, or 11). The terminators can have a sequence selected from any terminator sequence of SEQ ID NO: 1-20 (e.g. 2, 4, 6, 8, 10, or 12). Also disclosed are variant nucleic acid sequences having at least 60% or at least 65% or at least 70% or at least 75% or at least 80% or at least 85% or at least 90% or at least 95% or at least 97% or at least 98% (and, optionally, less than 100% in any embodiment) or 80-99% or 85-99% or 90-99% or 95-99% sequence identity to any of SEQ ID NOs: 1-20 or to a fragment of at least 75 or at least 100 or at least 150 or at least 200 or at least 250 or at least 300 or at least 500 contiguous nucleotides of any of SEQ ID NOs: 1-20, or any disclosed sequence. Sequences differing by at least one nucleotide from any of SEQ ID NO: 1-20, or from the fragments thereof, are variants of the particular reference sequence(s). In some embodiments the promoters have a functional promoter sequence within a sequence selected from any of SEQ ID NO: 1, 3, 5, 7, 9, or 11. In some embodiments the terminators can have a functional terminator sequence within a sequence selected from any of SEQ ID NO: 2, 4, 6, 8, 10, or 12. Also disclosed are nucleic acid sequences having at least 60% or at least 65% or at least 70% or at least 75% or at least 80% or at least 85% or at least 90% or at least 95% or at least 97% or at least 98% (and, optionally, less than 100% in any embodiment), or 80-99% or 85-99% or 90-99% or 95-99% sequence identity to a functional control sequence within a sequence of any of SEQ ID NOs: 1-20 or to a fragment of at least 75 or at least 100 or at least 150 or at least 200 or at least 250 or at least 300 or at least 500 contiguous nucleotides of any of SEQ ID NOs: 1-20, or any disclosed sequence. A functional control sequence is a promoter or terminator sequence having less than the full length sequence of any of SEQ ID NOs: 1-20. In various embodiments the functional control sequence can at least substantially perform the function of a promoter or terminator sequence. In one embodiment the functional control sequence performs at least 50% or at least 60% or at least 70% or at least 80% of the activity of any full length promoter or terminator sequence disclosed herein.

A promoter is a regulatory region of DNA and can be located upstream (towards the 5' region) of a gene. The promoter provides a control point for regulated gene transcription. Any of the promoters disclosed herein can contain a transcription start site (TSS), a binding site for RNA polymerase, and optionally one or more general transcription factor binding sites. In some embodiments, the promoter can consist of two short sequences at about −10 and −35 positions upstream from the transcription start site. The sequence at −10 can be a Pribnow box, or the −10 element, and can consist of the six nucleotides TATAAT. The Pribnow box can be necessary for starting transcription in prokaryotes. In some embodiments the sequence at about −35 (the −35 element) consists of the six nucleotides TTGACA.

Any of the promoters of the invention can be constitutive or inducible promoters. A constitutive promoter is active under most environmental and developmental conditions. A constitutive promoter can be active regardless of external environment, such as light and culture medium composition. In some examples, a constitutive promoter is active in the presence and in the absence of a nutrient or other analyte. For example, a constitutive promoter may be a promoter that is active (mediates transcription of a gene to which it is operably-linked) under conditions of nitrogen depletion as well as under conditions in which nitrogen is not limiting (nitrogen replete conditions). "Inducible" promoters are active in response to particular environmental condition, such as the presence or absence of a nutrient, analyte, regulator, the presence of light, or other conditions.

Any of the promoter and/or terminator sequences disclosed herein (and any combination of them) can be operably linked to a heterologous coding or non-coding nucleic acid sequence. The promoter and terminator sequences disclosed herein can be used in any combination. Any promoter disclosed herein can be paired with or used with any terminator disclosed herein to initiate and terminate transcription at a polynucleotide, gene, or sequence of interest. For example, any promoter of SEQ ID NO: 1, 3, 5, 7, 9, or 11 can be used with any terminator of SEQ ID NO: 2, 4, 6, 8, or 10, in all possible combinations. Any promoter disclosed herein can be used to initiate transcription at a gene or polynucleotide sequence and can be paired with any terminator disclosed herein to terminate transcription at the polynucleotide, gene, or sequence of interest. In any embodiment the promoter and terminator can be located on the same nucleic acid molecule. In one embodiment the promoter and terminator can be used in any of the stated combinations to initiate and terminate transcription on a single polynucleotide, gene, or sequence of interest. In one embodiment SEQ ID NO: 1 or a variant thereof is used as a promoter, and SEQ ID NO: 2 or a variant thereof is used as the terminator. In one embodiment SEQ ID NO: 3 or a variant thereof is used as a promoter, and SEQ ID NO: 4 or a variant thereof is used as the terminator. In one embodiment SEQ ID NO: 5 or a variant thereof is used as a promoter, and SEQ ID NO: 6 or a variant thereof is used as the terminator. In one embodiment SEQ ID NO: 7 or a variant thereof is used as a promoter, and SEQ ID NO: 8 or a variant thereof is used as the terminator. In one embodiment SEQ ID NO: 9 or a variant thereof is used as a promoter, and SEQ ID NO: 10 or a variant thereof is used as the terminator. In one embodiment SEQ ID NO: 11 or a variant thereof is used as a promoter, and SEQ ID NO: 12 or a variant thereof is used as the terminator. Any of these combinations of promoters and terminators can be operably linked to a coding or non-coding sequence of a gene or nucleic acid sequence.

The invention also provides vectors containing at least one promoter and/or terminator disclosed herein, or a variant of a promoter and/or terminator disclosed herein. In various embodiments the vectors can be expression vectors or cloning vectors. The vectors can also comprise at least one polynucleotide sequence of interest. In some embodiments the vector can contain a selectable marker or reporter gene (e.g. a fluorescent markers or proteins, antibiotic resistance (e.g., blasticidin, bleomycin, etc.)), many of which are known in the art. In some embodiments, the vectors can be designed for the integration of one or more polynucleotide sequence(s) into a host cell genome. The polynucleotide sequence of interest can be a gene, a sequence to be expressed, or another polynucleotide sequence of interest. For example, the vectors may include flanking sequences designed for integrating transgenes into the genome of a target algal host cell. In other embodiments, vectors can be targeted for integration into an algal chromosomal sequence by including flanking sequences that allow homologous recombination into the chromosome or target, or for integration into endogenous host plasmids. In some embodiments where it may be advantageous to transform the chloroplast of a higher plant or alga, the vectors can be designed to have regions of sequences flanking the transgene that are homologous to chloroplast sequences to promote homologous recombination and integration of the sequence of interest. Further, a transformation vector can include sequences for site-specific recombination such as, but not limited to, lox sites on which the Cre recombinase acts. In various embodiments the vectors can contain any one or more of introns, enhancers, transit peptides, targeting signal sequences, 5' and 3' untranslated regions (UTRs), IRES, 2A sequences, promoter and/or terminator sequences, as well as other molecules involved in the regulation of gene expression that are useful in the design of effective expression vectors. In some embodiments, the expression vector can contain one or more enhancer elements. Any of the vectors or expression cassettes of the invention can be a linear or circular polynucleotide or DNA.

In some embodiments the vector can be an expression cassette comprising one or more promoters and/or terminators described herein, or variants of the promoters or terminators described herein. These cassettes can comprise one or more promoter and/or terminator sequence(s) operably linked to one or more polynucleotide(s), gene(s), or nucleic acid sequence(s) of interest, which can be coding or non-coding sequences. The polynucleotide, gene, or sequence of interest can be positioned downstream of a promoter sequence, which can be expressed. Both a promoter and terminator can be operably linked to the same polynucleotide, gene, or nucleic acid sequence of interest. The one or more polynucleotide(s), gene(s), or nucleic acid sequence(s) of interest can be coding sequence(s) or non-coding sequence(s), which can be either homologous or heterologous nucleic acid sequences. In one embodiment the polynucleotide, gene, or nucleic acid sequence of interest is a heterologous sequence.

Persons of ordinary skill know how to calculate the percent of "sequence identity" between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

As used herein, "exogenous" with respect to a nucleic acid or gene indicates that the nucleic acid or gene has been introduced (e.g. "transformed") into an organism, microorganism, or cell by human intervention. Typically, such an exogenous nucleic acid is introduced into a cell or organism via a recombinant nucleic acid construct. An exogenous nucleic acid can also be a "heterologous" nucleic acid, i.e. a sequence from one species introduced into another species. A heterologous nucleic acid can also be an exogenous synthetic sequence not found in the species into which it is introduced; a heterologous sequence can also be a nucleic acid sequence operably linked to another nucleic acid sequence that it is not operably linked to in Nature. Heterologous sequences can therefore be heterologous to an organism they are transformed into, or heterologous to a sequence they are operably linked to. For example, a promoter or terminator operably linked to a nucleic acid sequence (e.g. a sequence of interest) that it does not regulate in Nature or in a wild-type cell are heterologous sequences to each other. Promoters and terminators (among other sequences) are considered control sequences as used herein. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

The term "operably linked," as used herein, denotes a configuration in which a promoter, terminator, or other regulatory or control sequence is placed at an appropriate position relative to a polynucleotide sequence of interest (e.g. a coding sequence) such that the control sequence directs or regulates the expression of the coding sequence of a polypeptide and/or functional RNA. Thus, a promoter is in operable linkage with a nucleic acid sequence if it can mediate transcription of the nucleic acid sequence. Terminators in operable linkage can direct or regulate a termination of transcription.

When introduced into a host cell, an expression cassette can result in transcription and/or translation of an encoded RNA or polypeptide under appropriate conditions. In the case of both expression of trans genes and suppression of endogenous genes (e.g., by antisense or RNAi) one of ordinary skill will recognize that the inserted polynucleotide sequence need not be identical, and may be only substantially identical to a sequence of the gene from which it was derived.

The terms "promoter", "promoter region", or "promoter sequence" refer to a nucleic acid sequence capable of binding RNA polymerase to initiate transcription of a polynucleotide sequence or gene in a 5' to 3' ("downstream") direction. A polynucleotide or gene is "under the control of" or "regulated by" a promoter when the binding of RNA polymerase to the promoter is the proximate cause of said polynucleotide or gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and, preferably, other transcription factors, regulatory sequence elements such as cis-elements or enhancer domains that affect the transcription of operably linked genes. An "algal promoter" is a native or non-native promoter that is functional in algal cells.

"Regulatory sequence", "regulatory element", or "regulatory element sequence" or "control sequence" refers to a nucleotide sequence located upstream (5'), within, or downstream (3') of a coding sequence. Promoters and terminators are control sequences, but can also be referred to as regulatory sequences. Transcription of the coding sequence and/or translation of an RNA molecule resulting from transcription of the coding sequence are typically effected by the presence or absence of the regulatory sequence. These regulatory element sequences may comprise promoters, cis-elements, enhancers, terminators, or in trans sequence(s). Regulatory elements may be isolated or identified from Un Translated Regions (UTRs) from a particular polynucleotide sequence. Any of the regulatory elements described herein may be present in a chimeric or hybrid regulatory expression element. Any of the regulatory elements described herein or variants thereof may be present in a recombinant vector or construct of the present invention.

The term "terminator" or "terminator sequence" or "transcription terminator" as used herein refers to a regulatory section of genetic sequence that causes RNA polymerase to cease transcription. A terminator sequence can give rise to signals in a synthesized RNA transcript that triggers processes that release the transcript RNA from the transcriptional complex.

Example 1—Plasmid Construction

Plasmid DNA was constructed using native *Picochlorum* regulatory elements such as promoters, terminators, and introns, combined with selectable marker transgenes BSD (blasticidin resistance) and BleR (Zeocin™ resistance).

Vectors JV202, JV204, JV206, JV208 were synthesized to contain different promoters and terminators driving a BSD gene that was sequence optimized for *Picochlorum* sp. and contained introns (1 or 2) paired to the native control elements. Vectors according to Table 1 were synthesized. For JV202 the promoter of SEQ ID NO: 1 was paired with the terminator of SEQ ID NO: 2. For JV204 the promoter of SEQ ID NO: 3 was paired with the terminator of SEQ ID NO: 4. For JV206 the promoter of SEQ ID NO: 5 was paired with the terminator of SEQ ID NO: 6. For JV208 the promoter of SEQ ID NO: 7 was paired with the terminator of SEQ ID NO: 8.

TABLE 1

| JV202 | CP12-PTI_BSD_PicoOpt2 | SEQ ID NO: 13 |
| JV204 | CPP1-PTI_BSD_PicoOpt2 | SEQ ID NO: 14 |
| JV206 | FDX1-PTI_BSD_PicoOpt2 | SEQ ID NO: 15 |
| JV208 | RBCS1-PTI_BSD_PicoOpt2 | SEQ ID NO: 16 |

Promoters were taken from endogenous *Picochlorum* genes and used to construct the vectors. The "PTI" designation indicates that the promoter, terminator, and any introns present were included in the sequences, while "PT" indicates no introns were included. BSD refers to the coding sequence for blasticidin resistance. "PicoOpt2" indicates the BSD sequence was optimized for expression in *Picochlorum* sp., which was done using known methods. CP12 is Calvin Cycle protein CP12. CPP1 is a conserved predicted protein. Thus, for example, plasmid JV206 contained a promoter and terminator from *Picochlorum* sp. ferredoxin gene driving a blasticidin (BSD) gene containing the two native FDX introns.

Plasmids were also synthesized containing BLE (also referred to as ZeoR), which is the coding sequence for zeocin resistance, as shown in Table 2. For JV209 the promoter of SEQ ID NO: 1 was paired with the terminator of SEQ ID NO: 2, without taking the introns from the CP12 gene. For JV210 the promoter of SEQ ID NO: 3 was paired with the terminator of SEQ ID NO: 4, including the introns from the CP12 gene. For JV214 expression the promoter of SEQ ID NO: 5 was paired with the terminator of SEQ ID NO: 6, including the introns from the FDX1 gene. For JV215 expression the promoter of SEQ ID NO: 7 was paired with the terminator of SEQ ID NO: 8.

TABLE 2

| Nickname | Full name |
|---|---|
| JV209 | CP12-PT-ZeoR_PicoOpt2 SEQ ID NO: 17 |
| JV210 | CP12-PTI-ZeoR_PicoOpt2 SEQ ID NO: 18 |
| JV214 | FDX1-PTI-ZeoR_PicoOpt2 SEQ ID NO: 19 |
| JV215 | RBCS1-PT-ZeoR_PicoOpt2 SEQ ID NO: 20 |

Example 2

Transformation and screening of strains was accomplished according to the following procedure. *Picochlorum* sp. was cultured overnight (25° C., ~150 µE/m2/s, 1% CO2) in PM153 algal growth media (1 L aquarium salts+1.3 mL Proline A+1.3 mL Proline C+4.4 mM Urea; Proline A contains 90 mM FeCl3*6H2O, 90 mM Na2 EDTA*2H2O, 323 uM CoCl2*6H2O, 585 uM ZnSO4*7H2O, 302 uM CuSO4*5H2O, 7 mM MnCl2*4H2O, and 200 uM Na2MoO4*2H2O; Proline C contains 278 mM NaH2PO4*H2O, 2.23 mM thiamine HCl, 2.85 uM B12, and 15.4 uM biotin). The culture was pelleted and was washed three times with 385 mM sorbitol and resuspended to 1.5e9 cells/mL in sorbitol. 100 ul of the washed cells were mixed with 5 µg of linearized plasmid DNA in an ice-chilled 2 mm electroporation cuvette. The electroporation was done using a BioRad® GenePulser®. After electroporation, 1 mL of sorbitol was added to the cuvette, and cells were transferred to 10 mL of PM153 media. The culture was incubated at 25° C. overnight in dim light (5 uE/m2/s). 5e8 cells were spread onto PM153 agar media (with ½ agar and ½ salt) in 80 mm polystyrene petri dishes with 50 µg/mL Zeocin™ or 500 µg/mL blasticidin depending on the selectable marker. Plates were incubated at room temperature under constant light (~150 µE/m2/s and 1% CO2) until colonies were formed. Colonies were repatched onto the same selection, and colonies that survived secondary selection and grew into patches with substantial biomass were carried forward.

Example 3

This example presents the results of transformation of cells. Tables 3 and 4 show the number of colonies obtained following the above procedure with the indicated vector.

TABLE 3

| Nickname | Full name | Colonies that survived re-patching |
|---|---|---|
| JV202 | BSD_PicoOpt2_CP12-PTI | 16 |
| JV204 | BSD_PicoOpt2_CPP1-PTI | 6 |
| JV206 | BSD_PicoOpt2_FDX1-PTI | 7 |
| JV208 | BSD_PicoOpt2_RBCS1-PTI | 10 |

All transformations provided a substantial number of colonies formed, with the CP12 or Rubisco promoter, terminator, and intron showing the highest numbers of colonies formed. However, good transformation results were also obtained with the CPP1 promoter, as well as with the ferredoxin promoter.

TABLE 4

| Nickname | Full name | Colonies that survived re-patching |
|---|---|---|
| JV209 | ZeoR_PicoOpt2_CP12-PT | 3 |
| JV210 | ZeoR_PicoOpt2_CP12-PTI | 1 |
| JV214 | ZeoR_PicoOpt2_FDX1-PTI | 1 |
| JV215 | ZeoR_PicoOpt2_RBCS1-PT | 3 |

All vectors show effective expression of the encoded gene. Vectors having the promoter of SEQ ID NO: 1 and the terminator of SEQ ID NO: 2, and the promoter of SEQ ID NO: 7 with the terminator of SEQ ID NO: 8 showed particularly robust expression of the heterologous genes, as indicated by the number of colonies formed.

What is claimed is:

1. A nucleotide sequence comprising a promoter having at least 90% sequence identity to a nucleotide sequence selected from the group consisting of: SEQ ID NO: 1, 3, 5, 7, 9, and 11, and operably linked to a heterologous nucleotide sequence of interest.

2. A vector for transforming a microorganism comprising the nucleotide sequence of claim 1.

3. A microorganism comprising the nucleotide sequence of claim 1.

4. The microorganism of claim 3, wherein said microorganism is an algal microorganism that expresses the heterologous nucleotide sequence of interest.

5. The microorganism of claim 4, wherein said microorganism is a Chlorophyte microorganism.

6. The microorganism of claim 5, wherein the Chlorophyte microorganism is of the Class Trebouxiophyceae.

7. The microorganism of claim 6, wherein the Trebouxiophyceae microorganism is *Picochlorum* sp.

8. The nucleotide sequence of claim 1, further comprising a terminator sequence.

9. An expression cassette comprising the nucleotide sequence of claim 8.

10. The nucleotide sequence of claim 8, wherein said terminator sequence has at least 90% sequence identity to a terminator sequence selected from the group consisting of SEQ ID NO: 2, 4, 6, 8, 10, and 12.

11. The nucleotide sequence of claim 8 wherein:
   a. the promoter sequence has at least 90% sequence identity to the nucleotide sequence of SEQ ID NO: 1 and the terminator sequence has at least 90% sequence identity to the nucleotide sequence of SEQ ID NO: 2; or
   b. the promoter sequence has at least 90% sequence identity to the nucleotide sequence of SEQ ID NO: 3 and the terminator sequence hast at least 90% sequence identity to the nucleotide sequence of SEQ ID NO: 4; or
   c. the promoter sequence has at least 90% sequence identity to the nucleotide sequence of SEQ ID NO: 5 and the terminator sequence hast at least 90% sequence identity to the nucleotide sequence of SEQ ID NO: 6; or
   d. the promoter sequence has at least 90% sequence identity to the nucleotide sequence of SEQ ID NO: 7 and the terminator sequence hast at least 90% sequence identity to the nucleotide sequence of SEQ ID NO: 8.

12. The nucleotide sequence of claim 8 wherein:
   a. the promoter sequence has at least 90% sequence identity to the nucleotide sequence of SEQ ID NO: 9 and the terminator sequence has at least 90% sequence identity to the nucleotide sequence of SEQ ID NO: 10; or
   b. the promoter sequence has at least 90% sequence identity to the nucleotide sequence of SEQ ID NO: 11 and the terminator sequence hast at least 90% sequence identity to the nucleotide sequence of SEQ ID NO: 12.

13. A vector for transforming a microorganism comprising the nucleotide sequence of claim 11.

14. A microorganism comprising the vector of claim 13, wherein said microorganism is an alga.

15. The microorganism of claim 14, wherein said microorganism is a Trebouxiophyte microorganism.

16. An expression cassette comprising the nucleotide sequence of claim 10.

17. A method of transforming an algal cell comprising introducing a vector comprising the expression cassette of claim 16 into an algal cell and selecting for a transformant comprising said vector.

18. The nucleotide sequence of claim 1, wherein the heterologous sequence of interest encodes a polypeptide or a functional RNA.

19. A nucleotide sequence comprising a promoter having at least 90% sequence identity to a nucleotide sequence selected from the group consisting of: SEQ ID NO: 1, 3, 5, 7, 9, and 11, and operably linked to a nucleotide sequence encoding a protein or a functional RNA heterologous to *Picochlorum* sp.

20. The nucleotide sequence of claim 19, further comprising a nucleotide sequence having at least 90% sequence identity to a terminator sequence selected from the group consisting of SEQ ID NO: 2, 4, 6, 8, 10, and 12.

21. An expression cassette comprising the nucleotide sequence of claim 20.

22. An expression cassette comprising the nucleotide sequence of claim 20, wherein:
   a. the promoter sequence has at least 90% sequence identity to the nucleotide sequence of SEQ ID NO: 1 and the terminator sequence has at least 90% sequence identity to the nucleotide sequence of SEQ ID NO: 2; or
   b. the promoter sequence has at least 90% sequence identity to the nucleotide sequence of SEQ ID NO: 3 and the terminator sequence hast at least 90% sequence identity to the nucleotide sequence of SEQ ID NO: 4; or
   c. the promoter sequence has at least 90% sequence identity to the nucleotide sequence of SEQ ID NO: 5 and the terminator sequence hast at least 90% sequence identity to the nucleotide sequence of SEQ ID NO: 6; or
   d. the promoter sequence has at least 90% sequence identity to the nucleotide sequence of SEQ ID NO: 7 and the terminator sequence hast at least 90% sequence identity to the nucleotide sequence of SEQ ID NO: 8.

23. The nucleotide sequence of claim 11, wherein the promoter sequence has at least 90% sequence identity to the nucleotide sequence of SEQ ID NO: 1 and the terminator sequence has at least 90% sequence identity to the nucleotide sequence of SEQ ID NO: 2.

24. The nucleotide sequence of claim 11, wherein the promoter sequence has at least 90% sequence identity to the nucleotide sequence of SEQ ID NO: 7 and the terminator sequence has at least 90% sequence identity to the nucleotide sequence of SEQ ID NO: 8.

* * * * *